United States Patent
Neubauer et al.

(10) Patent No.: US 8,469,965 B2
(45) Date of Patent: Jun. 25, 2013

(54) TOOL FOR DETECTING PLANES OF A BONE AND ASSIGNED DATA PROCESSING METHOD

(75) Inventors: Timo Neubauer, Grasbrunn-Neukeferloh (DE); Manuel Millahn, München (DE)

(73) Assignee: Brainlab AG, Feldkirchen (DE)

( * ) Notice: Subject to any disclaimer, the term of this patent is extended or adjusted under 35 U.S.C. 154(b) by 526 days.

(21) Appl. No.: 12/774,889

(22) Filed: May 6, 2010

(65) Prior Publication Data
US 2010/0286508 A1 Nov. 11, 2010

Related U.S. Application Data

(60) Provisional application No. 61/224,242, filed on Jul. 9, 2009.

(30) Foreign Application Priority Data

May 6, 2009 (EP) ..................................... 09159534

(51) Int. Cl.
*A61B 17/58* (2006.01)
*A61B 17/60* (2006.01)
*A61F 2/00* (2006.01)

(52) U.S. Cl.
USPC ........................ 606/102; 606/86 R; 600/429

(58) Field of Classification Search
USPC .................... 606/86 R, 87–89; 600/424, 427, 600/429
See application file for complete search history.

(56) References Cited

U.S. PATENT DOCUMENTS
2005/0190380 A1* 9/2005 Plassky et al. ................ 356/614

FOREIGN PATENT DOCUMENTS
| EP | 1 889 584 | 2/2008 |
| WO | 2004/041097 | 5/2004 |
| WO | 2007/085085 | 8/2007 |

* cited by examiner

*Primary Examiner* — Andrew Yang
(74) *Attorney, Agent, or Firm* — Renner, Otto, Boisselle & Sklar, LLP

(57) ABSTRACT

The present application relates to a tool for detecting planes which are defined by anatomical landmarks, comprising a first and a second level abutment area for placing onto a body structure, wherein the first and second abutment areas have a predetermined position relative to each other, and comprising a tool marker device which has a stationary position relative to the first and second abutment areas.

16 Claims, 4 Drawing Sheets

TOOL FOR DETECTING PLANES OF A BONE AND ASSIGNED DATA PROCESSING METHOD

RELATED APPLICATION DATA

This application claims the priority of U.S. Provisional Application No. 61/224,242, filed on Jul. 9, 2009, which is hereby incorporated in its entirety by reference.

FIELD OF THE INVENTION

The present invention relates to a tool for detecting planes of a body structure (for example, bone) which are defined in particular by anatomical landmarks, in particular to a tool in an L-shaped form. The present invention also relates to a data processing method for processing data captured by means of the tool. The invention also relates to a program which performs the data processing method by means of a computer, and to a navigation system comprising such a computer.

BACKGROUND OF THE INVENTION

The present invention relates in particular to the field of computer-assisted navigation in surgery (IGS or "image-guided surgery"). Within this field, it is necessary to detect the spatial location of the bones using a surgical navigation system. A surgical navigation system and/or navigation system is understood to mean a system which consists of at least one marker device, a transmitter which emits electromagnetic waves and/or radiation and/or ultrasound waves, and a receiver which receives electromagnetic waves and/or radiation and/or ultrasound waves, as well as an electronic data processing device which is connected to the receiver and/or the transmitter, wherein the data processing device (for example, a computer) comprises a processor (CPU), a working memory, advantageously an indicating means (for example, a visual indicating means such as a monitor and/or an audio indicating means such as a loudspeaker) and advantageously a permanent data memory, wherein the data processing device processes navigation data relayed to it from the receiver and can advantageously output guidance information to a user via the indicating means. The navigation data can be stored in the permanent data memory and for example compared with data which has been provided in said memory beforehand. In order to detect the location of the bones, landmarks on the bone are for example tapped by means of a pointer, so as to communicate the location of the landmark to the navigation system, so as to be able to produce a three-dimensional image of the bone which shows the position of the bone. In short, the bone is registered with the aid of the navigation system. A pointer is a tool, in particular a rod, with a number of markers—advantageously, three markers—fastened to it, wherein the relative location between the markers and the tip of the pointer is known. Thus, by detecting the position of the markers, it is possible to determine where the tip of the pointer is situated. If the tip of the pointer is brought into contact with a landmark, the position of the landmark of the bone is thus known.

It is the function of a marker to be detected by a marker detection device (a detection device such as for example a camera or an ultrasound receiver) of the navigation system, such that its spatial position (i.e. location and/or alignment) can be ascertained. Such markers can be active markers. An active marker emits for example electromagnetic radiation and/or waves, wherein said radiation can be in the infrared, visible and/or ultraviolet spectral range. The marker can also however be passive, i.e. can for example reflect electromagnetic radiation from the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered—for example, cubic—shape.

A "reference star" refers to a device with a number of markers, advantageously three markers, attached to it, wherein the markers are attached to the reference star such that they are stationary and advantageously detachable, thus providing a known (and advantageously fixed) position of the markers relative to each other. The position of the markers relative to each other can be individually different for each reference star used within the framework of a surgical navigation method, in order to enable the corresponding reference star to be identified by a surgical navigation system on the basis of the position of the markers relative to each other. It is therefore also then possible for the objects (for example, instruments and/or parts of a body) to which the reference star is attached to be identified and/or differentiated from each other. In a surgical navigation method, the reference star serves to attach a plurality of markers to an object (for example, a bone or a medical instrument) in order to be able to detect the spatial position of the object (i.e. its location and/or alignment). Such a reference star in particular comprises a way of being attached to the object (for example, a clamp and/or a thread) and/or a holding element which ensures a distance between the markers and the object (in particular in order to assist the visibility of the markers to a marker detection device) and/or marker holders which are mechanically connected to the holding element and which the markers can be attached to. Where it is clear from the context, the term "reference star" can also refer to a reference star with at least one marker attached to it. Such a system consisting of a reference star and at least one marker can also be referred to as a marker star.

A marker device comprises at least one marker, preferably at least two or three markers, and can for example be a reference star, a pointer and/or an individual marker or a number of markers. A marker device which is attached (such that it is stationary) to the tool is also referred to here as a tool marker device. A marker device which is attached (such that it is stationary) to the body structure is also referred to here as a body structure marker device.

Detecting landmarks by means of pointers is time-consuming and extends the operation time and thus the burden on the patient.

When resecting the distal end of the femur in order to replace it with an implant, particular variable information about the distal end of the femur is required. This information is conventionally captured in such a way that a pointer is moved to the condyles in order to detect the most distal point in each case. A corresponding procedure is followed in order to detect the furthest posterior point on the posterior side of each of the condyles. This procedure is time-consuming.

SUMMARY OF THE INVENTION

It is an object of the invention to facilitate and in particular accelerate the detection of variables which describe the bone anatomy.

The above object is solved by the subjects of the independent claims. Advantageous developments follow from the sub-claims.

A tool is advantageously provided for detecting planes which in particular abut anatomical body structures, in particular bones (for example, the femur). The planes can in particular be defined by anatomical landmarks.

A landmark is a defined, characteristic point of an anatomical structure which is always identical or recurs with a high degree of similarity in the same anatomical structure of multiple patients. Typical landmarks are for example the epicondyles of a femoral bone or the tips of the transverse processes and/or dorsal process of a vertebra.

The planes (more specifically, their position or their position relative to each other) in particular describe a particular shape property of the body structure (for example, the femur) or represent said shape, which provide a surgeon with important information about the preferred shape and size of an implant. They are therefore also referred to here as "shape representatives".

Shape representatives represent a characteristic aspect of the shape of the anatomical structure. Examples of shape representatives are straight lines, planes or geometric figures. Geometric figures can be one-dimensional such as for example axes or circular arcs, two-dimensional such as for example polygons and circles, or three-dimensional such as for example cuboids, cylinders and spheres. The relative position between the shape representatives can be described in reference systems, for example by coordinates or vectors, or can be described using geometric variables such as for example length, angle, area, volume and proportions. The characteristic aspects which are represented by the shape representatives are for example symmetry properties which are represented for example by an axis of symmetry. Another characteristic aspect is for example the direction of extension of the anatomical structure which is for example represented by a longitudinal axis. Another characteristic aspect is for example the cross-sectional shape of an anatomical structure which is for example represented by an ellipse. Another characteristic aspect is for example the surface shape of a part of the structure which is for example represented by a plane or a hemisphere. The characteristic aspect represents in particular an abstraction of the actual shape or an abstraction of a property of the actual shape (such as for example the symmetry property or longitudinal extension). The shape representative in particular represents this abstraction.

In order to detect the planes, abutment areas are provided in accordance with the invention which are preferably likewise planar (level). The abutment areas can however also be curved and can for example comprise concave portions in order to accommodate prominent parts of the bone. The tool preferably comprises two abutment areas, i.e. a first and a second abutment area. It can however also comprise more abutment areas. The abutment areas preferably have a predetermined (known) and stationary position relative to each other; in particular, the planes defined by the abutment areas preferably enclose a predetermined (known) angle relative to each other. The angle can be obtuse or acute. It is preferably a right angle. The plane in which the in particular planar abutment area lies is defined by this abutment area.

The tool preferably also comprises a marker device. This marker device has a stationary (and known) position relative to the first and second abutment areas. The marker device can be detachable. When connected, however, it is preferably—as mentioned—stationary and fixed relative to the first and second abutment areas.

The tool preferably has an L-shaped form. This means in particular that the two abutment areas do not intersect. This has the advantage that the tool can be introduced into the space between the body structures which is often very limited and difficult to access. A confined space exists for example between the femur and the tibia.

Advantageously, at least one of the abutment areas, for example the second abutment area, comprises a cavity. This cavity preferably interrupts a front-facing end of the abutment area, thus providing two front-facing end parts between which the cavity is situated. The cavity preferably extends from the front-facing end towards the other abutment area. The cavity extends for example from the front-facing end of the second abutment area, which faces away from the first abutment area, towards the first abutment area. This extension of the cavity is referred to as an extension in the longitudinal direction. This extension of the cavity in the longitudinal direction preferably relates to the majority of the length of the abutment area (for example, the second abutment area), for example to more than 50%, 70%, 80% or 90% of the length of the abutment area, or passes completely through it and ends in the first abutment area. The width of the cavity preferably occupies more than ¼ and/or less than ¾ of the overall width of the abutment area in which the cavity is situated. The cavity is preferably larger than 1 cm and/or smaller than 10 cm, in particular larger than 2 cm and/or smaller than 8 cm.

The cavity serves for example to place the two parts of the abutment area, which are separated by the cavity, onto the medial part of a condyle of the femur and the lateral, preferably posterior, part of a condyle of the femur, respectively, wherein the cavity leaves room for the cruciate ligaments. The width of the cavity is thus preferably formed so as to be able to accommodate the cruciate ligaments.

A holding grip is preferably attached to one of the abutment areas. The holding grip is preferably attached to the side of the abutment area which points away from the other abutment area. A marker device is preferably attached to the same abutment area as the holding grip.

The marker device, which is attached to one of the abutment areas, preferably extends away from said abutment area in such a way that it also extends away from the other abutment area, i.e. the marker device in particular extends away from both abutment areas.

The tool preferably comprises pressure sensors on the sides of the abutment areas which face towards each other. The pressure sensors are preferably provided in predetermined regions in which, when the tool is correctly placed onto the bone, a pressure contact with the bone is expected. These pressure sensors are preferably restricted to these regions. The tool preferably comprises a device for communicating the pressure sensor signal to a detector which is in particular part of a navigation system. In accordance with another embodiment, a number of pressure sensors are provided in an abutment area, so as to detect the pressure in a planar resolution. In this way, it is possible to determine whether or not the region in which a pressure has been detected matches the region to be expected. These pressure signals can then be communicated, so as to generate—with the aid of the navigation system—in particular guidance signals for the surgeon as to whether there is a pressure contact in the expected regions of the abutment area or whether the pressure contact exists in other regions. This makes it easier for the surgeon to handle the tool. Data which describes the regions to be expected, in which the pressure is supposed to occur, can be provided to the navigation system. The data can in particular be obtained from x-ray recordings or CT images and supplied to the navigation system. The expected region is in particular a region for which a contact with a prominent part of the bone, in particular a prominent landmark, is for example expected on the basis of bone data. Bone data describes the shape of the bone, for example on the basis of x-ray recordings and CT recordings.

The invention also relates to a data processing method which is in particular performed with the aid of a computer, i.e. the data to be processed is preferably supplied to a computer which then processes it (for example by performing a calculation or a determination).

The method in accordance with the invention is thus in particular a data processing method. The data processing method is preferably performed using technical means, in particular a computer. The computer in particular comprises a processor and a memory in order to process the data, in particular electronically. The calculating steps described are in particular performed by a computer. Steps of defining for example regions or values are in particular steps of determining data within the framework of the technical data processing method, in particular within the framework of a program. Modifying steps in particular represent modifying the data by means of the computer. Ascertaining steps in particular comprise retrieving values which are provided at an interface of the computer and have been generated using technical means, such as for example a scanning device. These values are in particular converted by the interface into data which can be processed by the computer.

Where data, regions, ranges or images are "provided", this means that they are ready for use by the method in accordance with the invention. The data can achieve this state of being "provided" by for example being captured (for example by analysis apparatuses) or by being input (for example via interfaces). The data can also have this state by being stored in a memory (for example a ROM, CD and/or hard drive) and thus ready for use within the framework of the method in accordance with the invention. The data can also have been determined, in particular calculated, in a step of the method before being provided, in particular before being stored.

The present invention relates in particular to a data processing method for determining the position of the tool relative to the body structure. When placing the tool onto the body structure, in particular a bone, the position is variable. In particular, the position is variable until a position criterion is fulfilled, as explained in more detail further below.

Preferably, tool marker position data is also provided. This marker position data describes the position of the tool marker device. This position is for example described in a reference system of the navigation system which detects the markers of the tool marker device.

The position which is described by the tool marker position data can change in the course of time. In particular, the tool marker position data can, at a particular point in time, be such that the position criterion described further below is fulfilled. With the aid of tool marker position data, it is thus in particular also possible to detect a change in the position of the tool marker device. In particular, the tool marker position data describes the positions of the tool marker device at different points in time.

Preferably, body structure marker position data is also provided. It describes the position of the body structure marker device, in particular in a reference system of the navigation system, in particular in the same reference system of the navigation system as that in which the position of the tool marker device is also described by the tool marker position data. The position of the body structure marker device can also change, and the body structure marker position data in particular describes the possibly changing position at different points in time. It preferably describes the positions at the same points in time as those at which the tool marker position data describes the positions of the tool marker device.

Shape data (in particular, axis data) is preferably also provided which describes the position of a shape representative, in particular an axis, in particular the longitudinal axis of the bone (for example, the mechanical axis of the femur), in particular relative to the body structure marker device and/or in the reference system of the navigation system. This shape data, in particular axis data, can also be detected by means of a pointer and then provided to the method in accordance with the invention.

If the position criterion is fulfilled, then the tool marker position data and the body structure marker position data which obtain when the criterion is fulfilled are determined. In particular, the tool marker position data and the body structure marker position data which obtain at the point in time when the position criterion is or was fulfilled are stored. The tool marker position data which fulfills said position criterion in the aforesaid way is referred to here as the criterion tool marker position data. The body structure marker position data which fulfills the position criterion in the aforesaid way is referred to as the criterion body structure marker position data.

Body structure data is preferably also provided which describes the relative position of the body structure marker device relative to at least a part of the body structure, in particular relative to a part of the surface of the body structure.

The relative position of the first and/or second abutment area relative to at least the part of the surface of the body structure for which the relative position relative to the body structure marker device is determined by the body structure data is preferably determined on the basis of the criterion tool marker position data and the criterion body structure marker position data and on the basis of the tool data and the body structure data. In this way, it is possible to determine how the first and/or second abutment area is lying relative to the body structure when the position criterion is fulfilled. Alternatively or additionally, the relative position of the first and/or second abutment area relative to the shape representative (for example, the mechanical axis) which obtains when the position criterion is fulfilled can be determined on the basis of the shape data, the tool data and on the basis of the criterion tool marker position data and the criterion body structure marker position data.

As discussed above, it is thus possible to determine how—if the position criterion is fulfilled—the first and/or second abutment area is lying relative to the shape representative (mechanical axis) and/or relative to the body structure (in particular, relative to a part of the surface of the body structure) when the position criterion is fulfilled. In particular for the surgeon, this information fulfils the same purpose as determining the position of the joint lines relative to the body structure or relative to the mechanical axis. However, the data processing method described allows the surgeon to determine this essential position information more easily.

The present invention relates in particular to a data processing method for determining a distance. This determined distance can in particular (also) be used to select an implant.

The distance is referred to here as the transverse distance. The distance to be determined lies between a first landmark (for example, the anterior cortex landmark of the femur) and one of the abutment areas of the tool (in particular, the second abutment area). This abutment area preferably lies on the side of the bone opposite said first landmark. In other words, the bone thus lies between the first landmark and the abutment area (the second abutment area). Since the (first and/or second) abutment area is preferably planar, there is a region of contact—in particular, a punctiform region of contact—between the abutment area and a protruding region of the bone which in particular corresponds to a landmark.

A series of data is preferably provided to the data processing method, such that it can determine the transverse distance from this. Preferably, said tool data—which describes the position of the first and second abutment area of the tool relative to each other and/or relative to the tool marker device—is provided. If the tool comprises additional abutment areas, then their position is preferably likewise described by the tool data.

Landmark data is preferably also provided. It describes in particular the position of the first landmark (for example, the anterior cortex landmark). This position can for example likewise be described in the aforementioned reference system of the navigation system. The landmark data can for example be detected by means of a pointer and then provided to the method in accordance with the invention.

On the basis of the data provided, a determination is made by means of the computer as to whether the tool fulfils a position criterion which relates to the position of the tool relative to the shape representative, in particular relative to the axis (for example, the mechanical axis of the femur). The position criterion is for example that one of the abutment areas, for example the second abutment area, assumes a particular orientation relative to the shape representative, in particular relative to the axis, and is in particular parallel to the axis, and/or that the axis is normal with respect to a plane defined by the abutment areas.

If a variable (referred to in the following as the relative variable) which describes the relative position between the first landmark and at least one of the abutment areas, in particular the second abutment area—in particular relative locations, a relative angle or relative distance, or a distance, in particular the transverse distance between the first landmark and the second abutment area—is determined, then the position criterion is preferably that the axis should be normal with respect to the plane defined by the first abutment area.

In order to verify whether the position criterion is fulfilled, the position of the first abutment area is for example calculated on the basis of the tool data and the tool marker position data. If this position is then known, the position of the (first) plane which is defined by the first abutment area is also known. The position of the axis (for example, the mechanical axis of the femur) is known from the axis data, such that it is possible to determine the relative position of the axis relative to the (first) plane. It is in particular possible to determine whether or not the axis is normal with respect to the (first) plane. The relative position of the first and/or second abutment area relative to the marker device is preferably described, by means of the tool data, by the position of the normal axis of the first and/or second abutment area relative to the marker device.

If the position criterion is fulfilled, the relative variable—in particular, the transverse distance—is then calculated. In particular, the marker position data which obtains or obtained at the point in time when the position criterion is or was fulfilled is used to calculate the relative variable, in particular the transverse distance.

In accordance with one embodiment, marker position data which may be constantly changing is then provided to the data processing method, and the marker position data which is indicated on the basis of the axis data as fulfilling the position criterion is singled out.

The axis data provided can in turn be calculated from other data. In the case of the femur, for example, the axis can in particular be determined from a point of rotation about which the neck axis is rotated and from the distal axis point which in particular matches the end of the marker channel and/or a landmark such as the trochlea ossis femoris. The axis is obtained from the connection between the point of rotation and the landmark. This determination can also be part of the data processing method. The points or landmarks necessary for this (for example, the point of rotation and the trochlea ossis femoris) are then provided to the data processing method.

The position of the intersection point between the axis and one of the abutment areas, in particular the first abutment area, is preferably calculated. This position can be calculated in the aforesaid reference system of the navigation system. The intersection point calculated in this way can in turn be used to calculate a joint line on the basis of said intersection point. The joint line likewise serves as a reference point for the surgeon to position an implant. The joint line is determined in such a way that a perpendicular is dropped from said intersection point onto the second abutment area. The perpendicular corresponds to the joint line.

The aforementioned transverse distance is preferably calculated, by means of the data processing method, in such a way that a perpendicular is dropped from the first landmark onto the second abutment area. The length of the perpendicular is then the transverse distance.

In addition to the transverse distance or as an alternative to the transverse distance, another relative variable is preferably also calculated, in particular a longitudinal distance. This is the shortest distance from the transverse perpendicular and said intersection point which is obtained from the axis and the first abutment area. This longitudinal distance likewise serves the surgeon in selecting the implant.

In addition to the aforesaid position criterion, a verification is preferably made as to whether another condition is fulfilled. This condition is the contact between the tool and the bone, in particular between a predetermined part (at least one of the two abutment areas) of the tool and a desired (predetermined) part of the bone (a prominent landmark). For this purpose, contact data is preferably provided to the data processing method which indicates whether or not there is a contact. In particular, it indicates whether the region of contact matches a landmark, as is desired. As described above, the contact can be determined by means of pressure sensors in the tool. The pressure sensors preferably indicate the contact in a predetermined region of the abutment areas. The bone data preferably also comprises information in order to be able to verify whether the contact with the desired part of the bone has been established. Alternatively, this can be performed in such a way that the operator (surgeon) communicates to the data processing method via a user interface (for example, a keyboard) that a contact between the tool and the bone, in particular between a predetermined part of the tool and the desired part of the bone, is established. If the contact data is for example provided in the way described above, then it is verified by the data processing method. If the contact data indicates a contact, in particular between the predetermined part of the tool and the desired (predetermined) part of the bone, the relative variable—in particular, the transverse distance—is calculated. In other words, the provided data which is valid at the point in time when the contact data indicates a contact, in particular a contact between the predetermined part of the tool and the desired (predetermined) part of the bone, and when the position criterion is fulfilled, is used to calculate the transverse distance. If the predetermined part of the tool—for example, a part of the first and second abutment area, respectively—is respectively in contact with a predetermined part of the bone, then this is an indication that the tool has been correctly placed onto the bone.

The signals detected by a pressure sensor can for example be communicated to the navigation system via radio, in order to be processed by the data processing method in accordance with the invention.

The data processing method preferably generates first guidance information which (like all the guidance information) is preferably output by means of a first guidance signal. This guidance information describes the relative variable, in particular the calculated transverse distance and/or longitudinal distance.

Second guidance information is preferably also generated by the data processing method. This second guidance information describes the orientation of the second abutment area relative to the axis. In this way, it is possible to indicate to an operator (surgeon), via guidance signals which indicate the second guidance information, whether or not the position criterion is fulfilled.

The invention is preferably also directed to a program which, when it is running on a computer or is loaded onto a computer, causes the computer to perform the data processing method.

The invention is preferably also directed to a navigation system which comprises a computer onto which the aforesaid program is loaded or on which the aforesaid program is running. In addition to the computer, the navigation system preferably comprises a detection device for detecting the marker device of the tool, so as to generate the marker position data. It preferably also comprises a user interface, in particular for inputting the contact data. It preferably also comprises a user interface (monitor, loudspeaker, etc.) for outputting acoustic and/or visual and/or tactile guidance signals such as those mentioned above. It preferably also comprises a data interface for supplying the other data mentioned to the computer. A memory is in particular provided in order to store said data and provide it to the data processing method.

DETAILED DESCRIPTION

Figures 1, 2A:
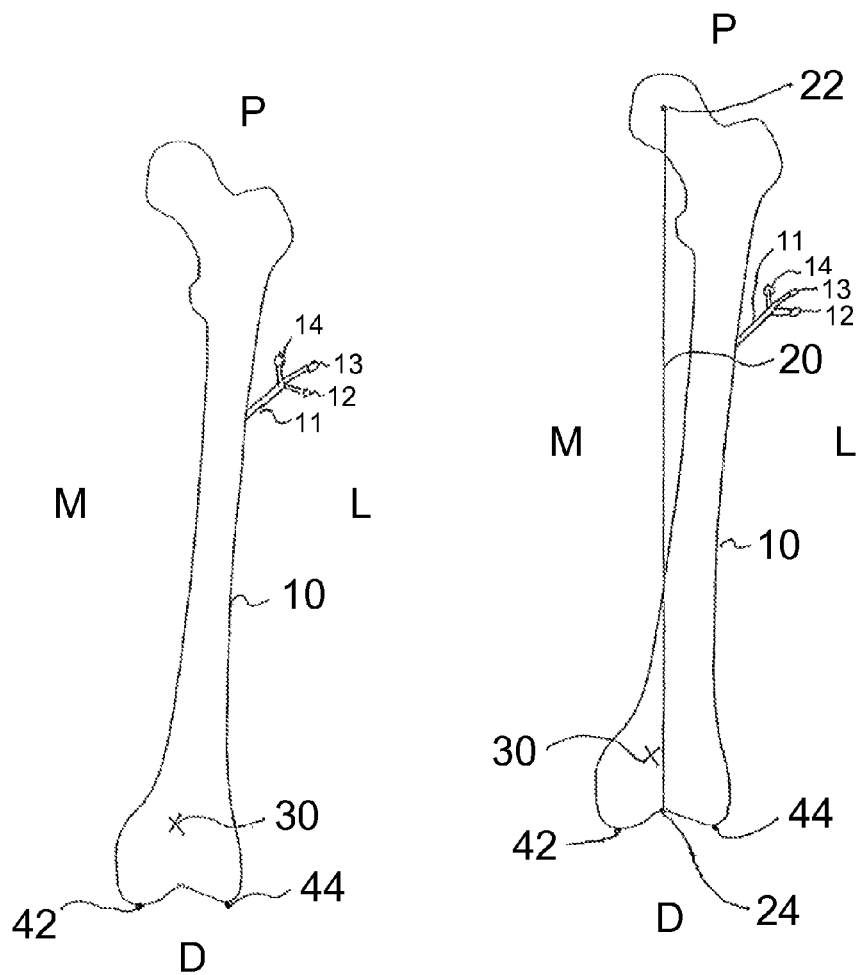
FIG. 1 shows a femur from the A-P viewing direction (anterior-posterior viewing direction).
FIG. 2a shows the femur of FIG. 1, with its mechanical axis indicated.

FIG. 1 shows a femur from the A-P viewing direction. It is a left femur. The letter "M" stands for "medial". The letter "L" stands for "lateral". The letter "P" stands for "proximal", and the letter "D" stands for "distal". The letter "P" stands for "proximal" when used opposite the letter "D"; if is used opposite the letter "A", it stands for "posterior", wherein "A" stands for "anterior".

Figure 2B:
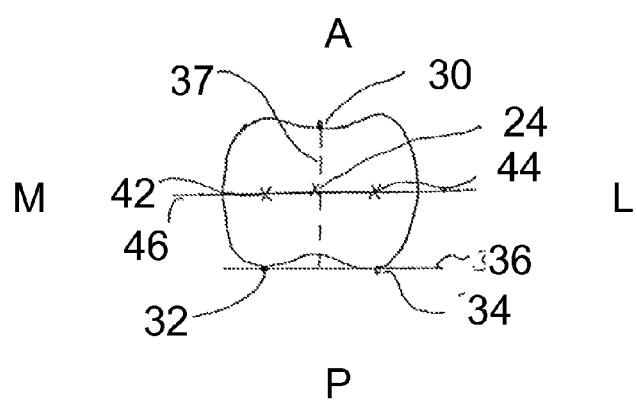
FIG. 2b shows a view of the distal end of the femur from the distal-proximal direction.

The teaching of the invention relates to detecting characteristic variables of the distal end of the femur. To this end, the anterior cortex point 30 is detected as a landmark by means of a pointer in the prior art. The reference signs 42 and 44 denote a medial-distal end and a lateral-distal end of the condyles, respectively. In order to detect these points 42 and 44, a series of points in the region of the distal ends of the two condyles are tapped by means of a pointer in the prior art, so as to determine the furthest distally lying point as the point 42 and 44, respectively. However, this is time-consuming. The points 42 and 44 represent examples of prominent landmarks which are supposed to come into contact with the (first) abutment area of the tool. By connecting the points 42 and 44, the joint line is obtained in the case of extension. The joint line in the case of flexion is obtained by connecting the points 32 and 34 (see FIG. 2b).

FIG. 2a shows the mechanical axis 20 being determined. To this end, the centre of rotation 22 of the femur is determined in the joint socket in a known way. This centre of rotation 22 is connected to the distal axis end point. The point of rotation 22 is thus connected to the distal axis point 24. The distal axis point 24 can also be seen in FIG. 2b.

In accordance with the prior art, the joint line is important to the surgeon for planning the implantation of an implant, if the distal end of the femur is being resected. A line 37, which is indicated by a broken line, is proximal with respect to the (extension) joint line 46. This is obtained in a known way by connecting the anterior cortex point 30 to the (flexion) joint line 36. The (flexion) joint line 36 is obtained in a similarly known way by connecting two points which lie the furthest posteriorly on each of the two condyles. In order to ascertain these posterior condyles points 32 and 34, a series of points on the condyles are likewise scanned in the prior art, and the one which lies the furthest posteriorly is selected in each case. This is also time-consuming. The points 32 and 34 represent examples of prominent landmarks which are supposed to come into contact with the (second) abutment area. The joint line 46 which obtains in the case of extension, and the joint line 36 which obtains in the case of flexion, represent important reference points for the surgeon in choosing the implant—in particular, their position relative to the bone.

Figure 3:
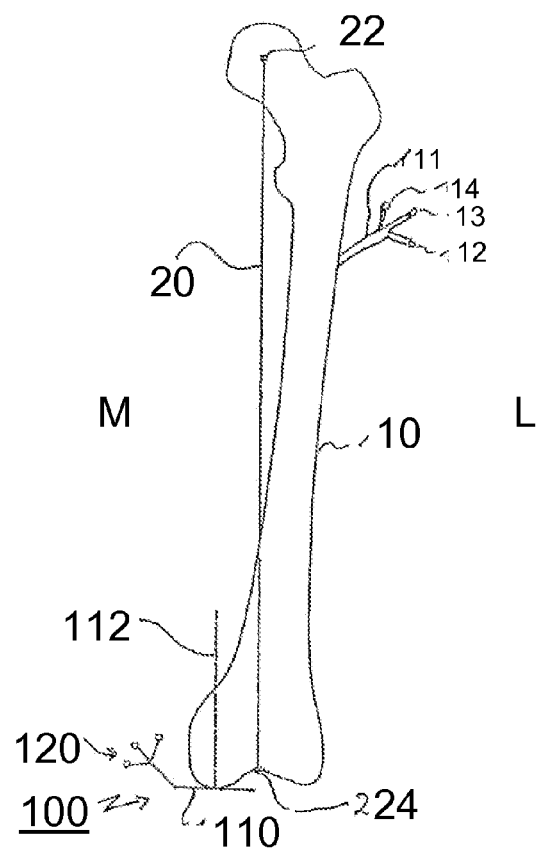
FIG. 3 again shows a femur from the A-P viewing direction, together with the tool in accordance with the invention.
Figure 5:
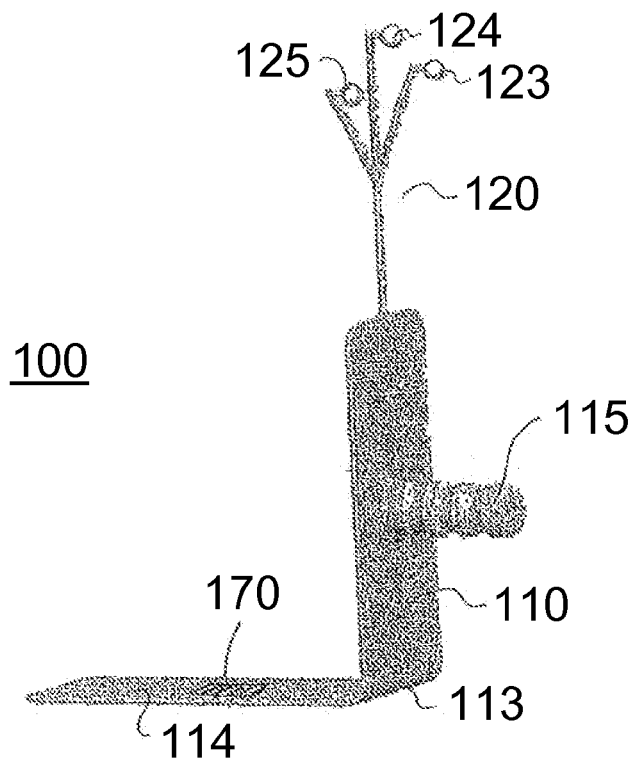
FIG. 5 shows a first embodiment of the tool in accordance with the invention.
Figure 6:
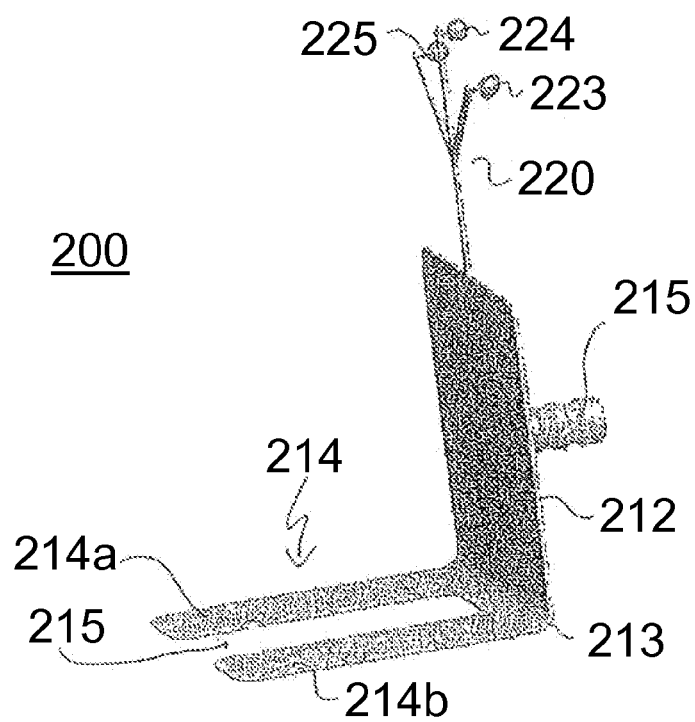
FIG. 6 shows a second embodiment of the tool in accordance with the invention.

FIG. 3 shows the tool 100 in accordance with the invention being used to ascertain characteristic planes of the distal end of the femur. The tool 100, which in particular has an L-shaped form as can be seen in FIGS. 5 and 6, is placed on the medial distal end of the femur via a first abutment area 110, such that the first abutment area 110 is in contact with the distal condyle point 42 which in this example represents the prominent landmark which defines the region of contact in contact with the first abutment area 110, wherein the tool 100 is also aligned such that a normal 112 onto the first abutment area 110, which is level, runs parallel to the mechanical axis 20.

Figure 4:
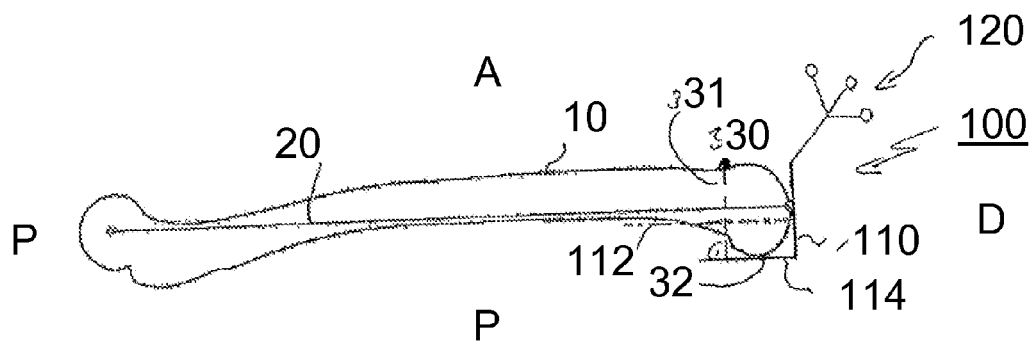
FIG. 4 shows the femur from the M-L viewing direction, together with the tool in accordance with the invention.

FIG. 4 shows the situation of FIG. 3, from the M-L viewing direction. The tool 100 (as shown in FIG. 5) is placed onto the femur 10 in the same way as in FIG. 3. It can also be seen that the second abutment area 114 abuts the posterior end of the medial condyle and is thus in contact with the point 32 which can be seen in FIG. 2b. The point 32 represents an example of a prominent landmark which determines the region of contact in contact with the second abutment area 114. In the example shown, each of the abutment areas is in contact with only one prominent landmark. Preferably, each abutment area is in contact with at least one (prominent) landmark. However, it can also be desirable for more than one landmark to be in contact with the abutment area.

It can likewise be seen in FIG. 3 that the second abutment area 114 runs parallel to the mechanical axis 20. Since the two abutment areas 110 (first abutment area) and 114 (second abutment area) are orthogonal with respect to each other, a normal 112 of the abutment area 110 is thus also parallel to the mechanical axis.

A reference star 120 can likewise be seen in FIGS. 3 and 4, which as a tool marker device serves to determine the position of the tool 100 by means of a navigation system.

A reference star 11 is also shown in FIGS. 1, 2a and 3 which serves as a body structure marker device and is attached such that it is stationary relative to the bone 10. The reference star 11 comprises the marker spheres 12, 13 and 14.

FIG. 5 shows the tool 100 in accordance with the invention, in which the abutment areas 110 and 114 form an L shape and are perpendicular to each other. The two abutment areas 110 and 114 are connected to each other by a curved region 113. A manual grip 115 allows the tool 100 to be handled. The tool shown in FIG. 5 comprises a reference star 120 at the front-facing end of the abutment area 110, where it protrudes in a longitudinal extension of the abutment area 110. The width of the abutment area 110 is in particular larger than 1/10 of the length of the abutment area 110 and/or in particular smaller than half the length of the abutment area 110. The width of the abutment area 110 is in particular larger than 1 cm and/or smaller than 10 cm. The length of the abutment area is in particular longer than 2 cm and/or shorter than 15 cm. The aforesaid sizes also apply in particular to the second abutment area 114. The thickness of the abutment areas is in particular larger than 0.1 mm and/or smaller than 5 cm, in particular smaller than 10 mm.

The tool in particular comprises metal, plastic and/or composite materials and/or ceramics as its materials.

The embodiment shown in FIG. 5 in particular serves to place the two abutment areas onto only one of the two condyles, more specifically onto a distal end and a posterior end of one of the condyles. The dimensions of the tool 100 shown in FIG. 5 are preferably chosen accordingly.

The position of an optional pressure sensor (which is formed to be planar) is indicated by 170.

FIG. 6 shows an alternative embodiment of the tool, which is provided with the reference sign 200. The tool 200 has a first abutment area 212 and a bifurcated second abutment area 214a and 214b, which are connected to each other in the curved region 213, which connects the two abutment areas, or in fact before the curved region 213. A cavity 215 separates the two parts of the abutment area 214a and 214b. The cavity 215 extends from the front-facing end of the abutment area 214—which faces away from the abutment area 212—towards the abutment area 212, more specifically towards the curved portion 213 of the tool 200. The cavity is in particular elongated, i.e. its profile in the direction of longitudinal extension towards the curved connecting portion is longer than its profile in the width direction. In particular, the profile of the cavity in the longitudinal direction is more than twice as large as the profile in the width direction and/or less than ten times the profile in the width direction. The cavity has a width which is in particular larger than 1 cm and/or smaller than 5 cm. The cavity is in particular configured such that it can accommodate the cruciate ligaments which run between the condyles, such that the second abutment area can be introduced between the femur and the tibia, while the cruciate ligaments are accommodated between the parts 214a and 214b of the abutment area.

Preferably, the same size specifications apply to the lengths of the tool 200 shown in FIG. 6, in particular to the lengths of the abutment areas 212 and 214, as apply to the lengths of the abutment areas 110 and 114. However, the width of the abutment areas 212 and 214 is preferably larger than the width of the abutment areas 110 and 114. In particular, values which are two or three times as large apply as the upper limits and lower limits for the tool 200 as compared to the tool 100, with respect to the width direction.

The manual grip 215, like the manual grip 115, allows the tool to be more easily handled. The reference stars are indicated by the reference sign 120 in FIG. 5 and by the reference sign 220 in FIG. 6. The individual marker spheres of the marker device 120 are denoted by the reference signs 123, 124 and 125 in FIG. 5, and the individual marker spheres of the marker device 220 are denoted by the reference signs 223, 224 and 225 in FIG. 6.

Figure 7:
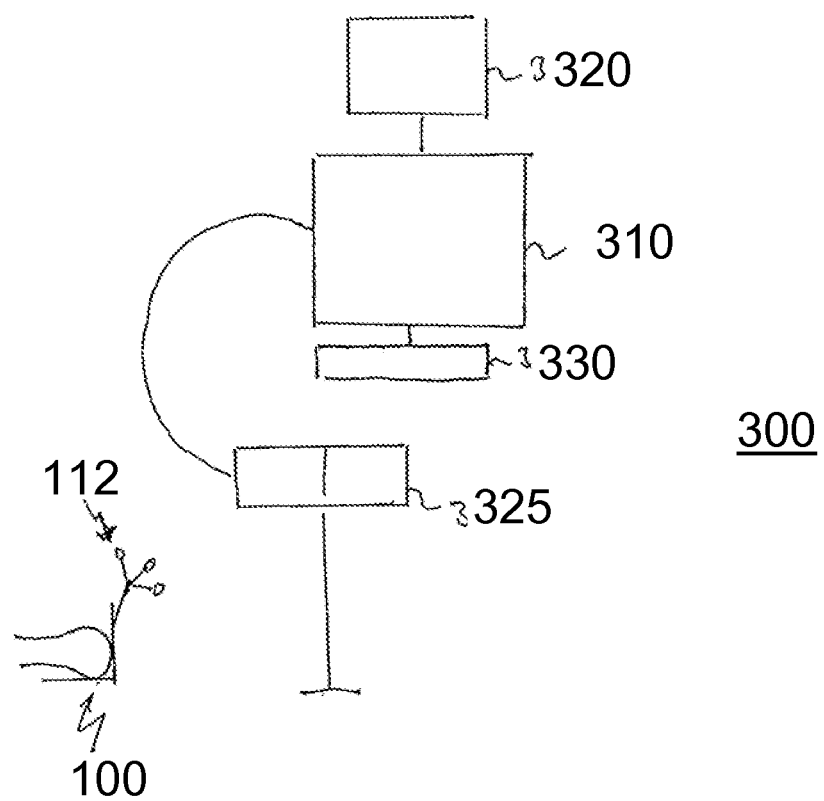
FIG. 7 shows a system in accordance with the invention, comprising a navigation system and the tool in accordance with the invention.

FIG. 7 shows a system in accordance with the invention, consisting of the tool 100 (or 200) and a navigation system 300. The navigation system 300 preferably comprises a computer 310, a monitor 320 and a detection device 325 which is connected to the computer 310. The detection device detects radiation emitted or reflected by the reference stars 11 and 120. The detection signals generated by the radiation are supplied to the computer 310 which calculates the position of the tool 100 in a reference system on the basis of them. The position can in particular be indicated on the monitor 320. The monitor 320 can also be used to indicate other guidance information. A keyboard or mouse 330 can also be provided as a user interface. In particular, the data processing method in accordance with the invention is running on the computer 310. The data processing method in particular determines the position of the tool and in particular verifies whether the normal with respect to the first abutment area 110 (or 212) is parallel to the mechanical axis. The position of the mechanical axis is either input via a user interface, or data is input which allows the position of the mechanical axis to be determined. The position of the point of rotation 22 and, for example with the aid of a pointer, the position of the trochlea point 24 are for example communicated to the navigation system. The data provided thus allows the position of the mechanical axis to be determined. The data thus provided to the system allows the position of the tool relative to the body structure, in particular the position of the first and/or second abutment area relative to the body structure and/or relative to the mechanical axis, to be determined for the scenario in which the position criterion is fulfilled. In particular, the available data allows a verification as to whether said position criterion is fulfilled and in particular allows the point in time at which said position criterion is fulfilled to be verified. The data relating to the position of the tool (the criterion tool marker position data) and the data relating to the position of the body structure (the bone) (the criterion body structure marker position data) which obtain at the point in time when the position criterion is or was fulfilled are then used to determine the relative position of the tool relative to the body structure and/or relative to the shape representative (the mechanical axis). The information about this relative position is preferably communicated to the surgeon as guidance information, for example using the user interface (the monitor 320).

The position of the anterior cortex point is preferably also communicated to the system. The data provided to the method or system in this way can be used to determine the distance between the anterior cortex point 30 shown in FIG. 4 and the second abutment area 114 (or 214). In particular, the perpendicular (transverse perpendicular) is dropped from the anterior cortex point 30 onto the abutment area 114, in order to determine the distance between the anterior cortex point 30 and the area 114. The variable thus ascertained is important to the surgeon for selecting a suitable implant, if the distal end of the femur is resected. This distance in particular is shown on the monitor 320. Dropping the transverse perpendicular 31 is indicated in FIG. 4 by a broken line.

The navigation system in particular also determines the orientation of the first abutment area 110 or 212 by means of the reference star. This orientation of the abutment area 110 then allows the aforesaid joint line to be determined. The joint line is in particular determined in such a way that it lies in the first abutment area 110 and runs normal with respect to the second abutment area 114 (or 214).

The aforesaid method steps are performed by the computer 310 which processes the provided data in order to calculate the desired variables, in particular the distance between the point 30 and the plane 114, and the position of the joint line. The distance between the transverse perpendicular 31 and the first abutment area 110 (or 212) is preferably also determined and in particular indicated.

In order to obtain the axis data, the mechanical axis of the femur can for example be determined by the following steps:
 a reference star is attached to the femur;
 the femur is pivoted in the joint socket, in order to calculate the point of rotation of the femoral head;
 the distal axis end point is recorded using a pointer;
 these two points are connected and referred to forthwith as the "mechanical axis";
 the abutment area 214 is inserted into the joint cavity and therefore abuts the medial and the lateral posterior side of the condyle;
 the L-shaped device is inserted until the abutment area 212 abuts the distal end of the femur;
 the L-shaped device is then rotated about the M-L axis and about the A-P axis;
 wherein the medial and the lateral posterior condyle and the distal end of the femur (possibly only a point) abut the abutment areas 214 and 212, respectively;
 the position of the normal axis with respect to the abutment area 212 is then calculated on the basis of the tool data and the marker position data and compared with the position of the mechanical axis—this is preferably achieved in two projections, namely the view in the M-L direction and the view in the A-P direction;
 as soon as the normal axis lies parallel to the mechanical axis in both observed views simultaneously, the location of the L-shaped device is stored;
 the location of the abutment area 214 provides a plane through the two most posterior points of the femur, wherein this plane is used to determine the internal/external rotation of the implant and/or bone sections required for implantation;
 the location of the abutment area 212 provides a plane through the most distal point of the femur, wherein this plane is used to navigate the distal section by which the length of the leg, the varus/valgus and the flexion/extension are determined.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electro-magnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A tool for detecting planes which are defined by anatomical landmarks, comprising:
 a first and a second level abutment area for placing onto a body structure, wherein the first and second abutment areas have a predetermined position relative to each other;
 a tool marker device which has a stationary position relative to the first and second abutment areas; and
 a pressure sensor which detects whether a pressure is being exerted in predetermined partial regions of the first and second abutment areas which lie on the mutually facing sides of the first and second abutment areas.

2. A data processing method for use with a tool for detecting planes which are defined by anatomical landmarks, the tool including a first and a second level abutment area for placing onto a body structure, wherein the first and second abutment areas have a predetermined position relative to each other, and a tool marker device which has a stationary position relative to the first and second abutment areas, the data processing method determining the variable position of the first and second abutment areas of the tool relative to the body structure, wherein the first abutment area abuts a first side of the body structure, and the second abutment area abuts a second side of the body structure, wherein the following data is provided:
 tool marker position data which describes the position of the tool marker device;
 body structure marker position data which describes the position of a body structure marker device which is attached to the body structure; and
 shape data which describes the position of a shape representative of the body structure, and wherein the following data processing steps are performed:
determining whether the position of the shape representative fulfills a position criterion which relates to the position of the shape representative relative to the first and/or second abutment area;
determining the tool marker position data and the body structure marker position data which obtain when the position criterion is determined to be fulfilled.

3. The data processing method according to claim 2, wherein the relative position between the shape representative and the first and/or second abutment area is determined on the basis of the determined tool marker position data and the determined body structure marker position data and on the basis of the shape data and tool data which describes the relative position of the first and/or second abutment area relative to the tool marker device, and/or the relative position between at least a part of the body structure and the first and/or second abutment area is determined on the basis of the determined tool marker position data, the determined body structure marker position data, the tool data and the body structure data which describes the relative position of the body structure marker device relative to at least the part of the body structure.

4. The data processing method according to claim 3, wherein contact data is also provided to the data processing method which indicates whether the abutment areas are in contact with the bone, and the transverse distance and/or the longitudinal distance is calculated if the contact is indicated by the contact data.

5. The data processing method according to claim 3, wherein first guidance information is generated which indicates the calculated transverse distance and/or longitudinal distance and/or wherein second guidance information is output which indicates the orientation of the second abutment area relative to the axis.

6. The data processing method according to claim 2, wherein:
tool data is provided which describes the relative position of the first and second abutment areas of the tool relative to the tool marker device;
landmark data is provided which describes the position of a first landmark in the reference system; the shape representative is an axis; the body structure is a bone; and
a variable which describes the relative position between the first landmark and at least one of the abutment areas is calculated on the basis of the determined tool marker position data and the determined body structure marker position data and on the basis of the tool data, wherein the variable is a transverse distance between the first landmark and the second abutment area which runs transverse to the axis.

7. The data processing method according to claim 6, wherein the position of the intersection point between the axis and the first abutment area is calculated, wherein a line which is referred to as the joint line is calculated by dropping a first perpendicular from the calculated intersection point onto the second abutment area.

8. The data processing method according to claim 6, wherein a second perpendicular is dropped from the first landmark onto the second abutment area in order to determine the transverse distance, and/or wherein a distance between the second perpendicular and the first perpendicular or the intersection point, which is referred to as the longitudinal distance and runs along the axis, is calculated.

9. A non-transitory computer readable medium comprising computer executable instructions, which, when executed by a computer, cause the computer to perform the data processing method according to claim 2.

10. A navigation system comprising a computer and the computer readable medium according to claim 9.

11. A system, comprising:
a tool for detecting planes which are defined by anatomical landmarks, comprising:
a first and a second level abutment area for placing onto a body structure, wherein the first and second abutment areas have a predetermined position relative to each other, and
a tool marker device which has a stationary position relative to the first and second abutment areas, wherein a planar surface of the first abutment area for placement onto the body structure is arranged at a non-zero angle relative to a planar surface of the second abutment area for placement onto the body structure;
the navigation system according to claim 10.

12. The system according to claim 11, wherein the first abutment area is positionally fixed relative to the second abutment area.

13. The system according to claim 11, wherein the tool has an L-shaped form, the first and second abutment areas forming an L-shape of the L-shaped form.

14. The system according to claim 11, wherein the second abutment area of the tool comprises a cavity which begins between two front-facing ends of the second abutment area of the tool which face away from the first abutment area of the tool and extends towards the first abutment area of the tool over a majority of the length of the second abutment area of the tool in the longitudinal direction.

15. The system according to claim 11, wherein the tool comprises a holding grip attached to a side of the first abutment area that points away from the second abutment area and/or wherein the marker device extends away from the side of the first abutment area that faces away from the second abutment area.

16. A system, comprising:
a tool for detecting planes which are defined by anatomical landmarks, comprising:
a first and a second level abutment area for placing onto a body structure, wherein the first and second abutment areas have a predetermined position relative to each other;
a tool marker device which has a stationary position relative to the first and second abutment areas; and
a pressure sensor which detects whether a pressure is being exerted in predetermined partial regions of the first and second abutment areas which lie on mutually facing sides of the first and second abutment areas; and
the navigation system according to claim 10.

* * * * *